(12) United States Patent
Huang et al.

(10) Patent No.: US 7,133,856 B2
(45) Date of Patent: Nov. 7, 2006

(54) BINARY TREE FOR COMPLEX SUPERVISED LEARNING

(75) Inventors: Jing Huang, Sunnyvale, CA (US); Richard A. Olshen, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 545 days.

(21) Appl. No.: 10/441,955

(22) Filed: May 19, 2003

(65) Prior Publication Data
US 2004/0019598 A1    Jan. 29, 2004

Related U.S. Application Data

(60) Provisional application No. 60/381,556, filed on May 17, 2002.

(51) Int. Cl.
*G06E 1/00* (2006.01)
(52) U.S. Cl. .......................... 706/21; 700/104
(58) Field of Classification Search .................. 706/21; 700/104
See application file for complete search history.

(56) References Cited

U.S. PATENT DOCUMENTS 5,263,117 A * 11/1993 Nadas et al. ................ 704/200

OTHER PUBLICATIONS

"An Introduction to Classification and Regression Tree (CART) Analysis", Roger J. Lewis, MD, PhD, Department of Emergency Medicine, Harbor-UCLA Medical Center, Torrance, CA, 2000.*

Leo Breiman, "Bagging Predictors," Machine Learning 24, 123-140 (1996).

Alfred Lin et al., "Clustering and the Design of Preference-Assessment Surveys in Healthcare," Health Services Research 34:5 Part I (Dec. 1999).3

Wei-Yin Loh et al., "Split selection methods for classification trees," Statistica Sinica 7(1997), 815-840.

(Continued)

*Primary Examiner*—David Vincent
*Assistant Examiner*—Mai T. Tran
(74) *Attorney, Agent, or Firm*—Lumen Intellectual Property Services, Inc.

(57) ABSTRACT

The present invention provides a powerful and robust classification and prediction tool, methodology, and architecture for supervised learning, particularly applicable to complex datasets where multiple factors determine an outcome and yet many other factors are irrelevant to prediction. Among those features which are relevant to the outcome, they have complicated and influential interactions, though insignificant individual contributions. For example, polygenic diseases may be associated with genetic and environmental risk factors. This new approach allow us consider all risk factors simultaneously, including interactions and combined effects. Our approach has the strength of both binary classification trees and regression. A simple rooted binary tree model is created with each split defined by a linear combination of selected variables. The linear combination is achieved by regression with optimal scoring. The variables are selected using backward shaving. Cross-validation is used to find the level of shrinkage that minimizes errors. Using a selected variable subset to define each split not only increases interpretability, but also enhances the model's predictive power and robustness. The final model deals with cumulative effects and interactions simultaneously.

16 Claims, 11 Drawing Sheets

OTHER PUBLICATIONS

Lee-Ming Chuang et al., "Sibling-based association study of the $PPAR\gamma_2$ Pro 12 Ala polymorphism and metabolic variables in Chinese and Japanese hypertension families: a SAPPHIRe study," J Mol Med (2001) 79:656-664.

Lorene M. Nelson et al., "Recursive partitioning for the identification of disease risk subgroups: a case-control study of subarachnoid hemorrhage,"J Clin Epidemiol vol. 51, No. 3 pp. 199-209, 1998.

Wei-Yin Loh et al., "Tree-structured classification via generalized discriminant analysis," Journal of the American Statistical Association, Sep. 1988, vol. 83, No. 403.

Philip A. Chou et al., "Optimal partitioning for classification and regression trees," IEEE Transactions on Pattern Analysis and Machine Intelligence, vol. 13, No. 4, Apr. 1991.

Louis Gordon et al., "Asymptotically efficient solutions to the classification problem," The Annals of Statistics 1987, vol. 6, No. 3, 515-533.

Gabor Lugcsi et al., "Consistency of data-driven histogram methods for density estimation and classification," The Annals of Statistics 1996, vol. 24, No. 2,687-706.

Trevor Hastie et al., "Gene saving' as a method for identifying distinct sets of genes with similar expression patterns," The electronic version can be found online at http//genomeniology.com/2000/1/2/research/0003/, Received Mar. 16, 2000, Revisions received May 16, 2000, Accepted May 18, 2000, Published Aug. 4, 2000.

* cited by examiner

BINARY TREE FOR COMPLEX SUPERVISED LEARNING

CROSS-REFERENCE TO RELATED APPLICATION

This application claims the benefit of a provisional patent application No. 60/381,556, filed May 17, 2002, the entire content and appendices of which are hereby incorporated herein by reference.

STATEMENT REGARDING FEDERALLY SPONSORED RESEARCH OR DEVELOPMENT

This invention was supported in part by the National Institutes of Health (NIH), grants No. HL54527 and No. CA59039. The U.S. Government may have certain rights in this invention.

COPYRIGHT NOTICE AND AUTHORIZATION

A portion of the disclosure of this patent document contains material which is subject to copyright protection. The copyright owner has no objection to the facsimile reproduction by any one of the patent document or the patent disclosure, as it appears in the U.S. Patent and Trademark Office patent file or records, but otherwise reserves all rights whatsoever.

BACKGROUND OF THE INVENTION

1. Field of the Invention

This invention relates generally to data mining. More particularly, it relates to a binary tree-structured classification and prediction algorithm and methodology for supervised learning on complex datasets, particularly useful in large-scale studies.

2. Description of the Related Art

In many real-world situations, multiple factors combine to determine outcome. Those factors have complicated and influential interactions, though perhaps small and insignificant individual contributions. Most of these individual contributions are so small that their effects could be masked easily by noise if they were considered only separately. One good example of such a situation is the association between polygenic disease and many genetic and environmental risk factors.

The affected status of an individual with such a polygenic disease is a result of interactions among multiple genes and environmental risk factors such as smoking, social stress, and diet. Asthma, hypertension (high blood pressure), type II diabetes and most cancers are polygenic diseases. They affect many people, yet their pathologies remain largely unknown. Limited knowledge tends to preclude researchers from creating effective screening tests or treatments.

One reason for such limited knowledge of pathologies is because, until now, most research on polygenic diseases focuses on identifying and evaluating effects of individual mutations. Each mutation is studied separately, ignoring the fact that the influence of multiple mutations can play a much larger role than the marginal contribution of any single mutation. The net result is a lack of understanding of complicated gene-gene and gene-environmental interactions that underlie most polygenic diseases. There is a continuing need in the art for a new and robust methodology for complex supervised learning where traditional approaches focusing on studying effects of individual factors have proven to be inadequate.

SUMMARY

The present invention addresses this need in the art by providing a binary tree-structured classification and prediction methodology that is particularly useful in large-scale studies, such as the research on polygenic diseases. The methodology includes a novel binary decision tree algorithm and applies to any situation in which a learning sample with features and outcome is given. According to an aspect of the invention, outcome is categorical and comprises two or several categories, for example, hypertensive, normotensive, or hypotensive. Features can also be categorical, for example, ethnicity, genotype at selected single nucleotide polymorphisms (SNPs), or real numbers, such as age, height, body mass index, and so on.

A principal goal is to predict outcome for a subject or candidate case where features are known but outcome is not. If the outcome is disease status or credit worthiness, then the present invention can also be used to define risk groups, especially high-risk groups. With conventional algorithms, this definition can be especially difficult when group membership is determined by complex combinations of features. However, the methodology disclosed herein provides superior performance even in complex situations, for example, predicting a complex human disease such as hypertension from SNPs and other variables.

The methodology is realized in a rooted binary decision tree having a set of terminal nodes that corresponds in a unique way to an element of a partition of a feature space. Each node (member) of the partition (group) has a category assigned in terms of an estimated Bayes rule for classification. At each internal node, a determination is made based on a criterion and the candidate observation to be classified is passed to the left or right daughter node of the internal node. When available features are insufficient to make that determination, an imputation is performed.

In some embodiments, the first step is to transform learning sample data, when necessary, from qualitative to quantitative. For example, genotype (feature) and disease status (outcome) are changed by successive application of a coding scheme and optimal scoring to a vector and a real number, respectively. Next, transformed features are ordered from worst to best in terms of prediction, and an optimally chosen subset of features is used to predict the (possibly transformed) outcome. For this reason, "features" are referred to hereinafter as "predictors."

The set of chosen predictors is pared down further by reapplication of an initial validated methodology until a single predictor remains. Among these nested subsets of predictors, the one with the best cross-validated reduction in a particular Gini index of diversity is chosen for splitting, according to reduction of the Gini index. Remaining variables are regressed on the optimally chosen scores. A larger tree than what will be reported is grown. As in CART®, the large tree is then pruned back to one with best-predicted prospective performance. Each terminal node has its own estimated Bayes rule.

As one skilled in the art would appreciate, the algorithm disclosed herein can be implemented in any suitable computer language. In an embodiment, the algorithm is implemented in the R language and integrated with a graphical user interface.

Still further objects and advantages of the present invention will become apparent to one of ordinary skill in the art upon reading and understanding the drawings and detailed description of the preferred embodiments disclosed herein.

DETAILED DESCRIPTION

As interest in complex human disease increases, there are increasing needs for methodologies that address issues such as gene-gene and gene-environment interactions in a robust fashion. The present invention provides a binary tree-structured classification tool that addresses such needs, particularly in predicting a complex human disease (hypertension) from single nucleotide polymorphisms (SNPs) and other variables. With a superior ability to handle combinations of predictors, the methodology disclosed herein extends beyond the traditional approach known as CART®, while retaining CART®'s simple binary tree structure. CART refers to Classification And Regression Trees where typically each split is defined by a single variable. CART® is a software package from Salford Systems.

According to an aspect of the invention, the methodology includes transforming categorical predictors to indicator variables, suitably scoring outcomes, backward selecting predictors from the least to the most "important," and constructing models while respecting family structures in the data. We successfully convert a problem of classification to one of regression without losing sight of classification. More specifically, with our methodology, each vector of predictor values can be located to one of several disjoint subgroups, that is, to a terminal node of a binary tree. Finding groups with high risk of disease may lend understanding to etiology and biological mechanism, as will be explained hereinafter in a later section.

In traditional classification trees, each split is on one feature alone. What is more, the set of features is not reduced in size before any splitting is attempted. Neither seems appropriate for polygenic disease, when no single gene is decisive and the "main effect" may be a gene by environment interaction; but most genes are irrelevant to the signal.

Algorithm

Our approach has the strength of both classification trees and regression. Although some underlying techniques are known, it is believed that our approach as a whole is utterly novel. The successive nodes of a rooted binary tree model are created with successive splits defined by respective linear combination of selected variables. Note a single variable can still be used to define the split. It is viewed as a special case of a linear combination. The linear combination is achieved by regression with optimal scoring. The variables are selected via a backward shaving procedure. Using a selected variable subset to define each split not only increases interpretability, but also improves the model robustness and prevents overfitting. The final model deals with cumulative effects and interactions simultaneously.

Figure 1:
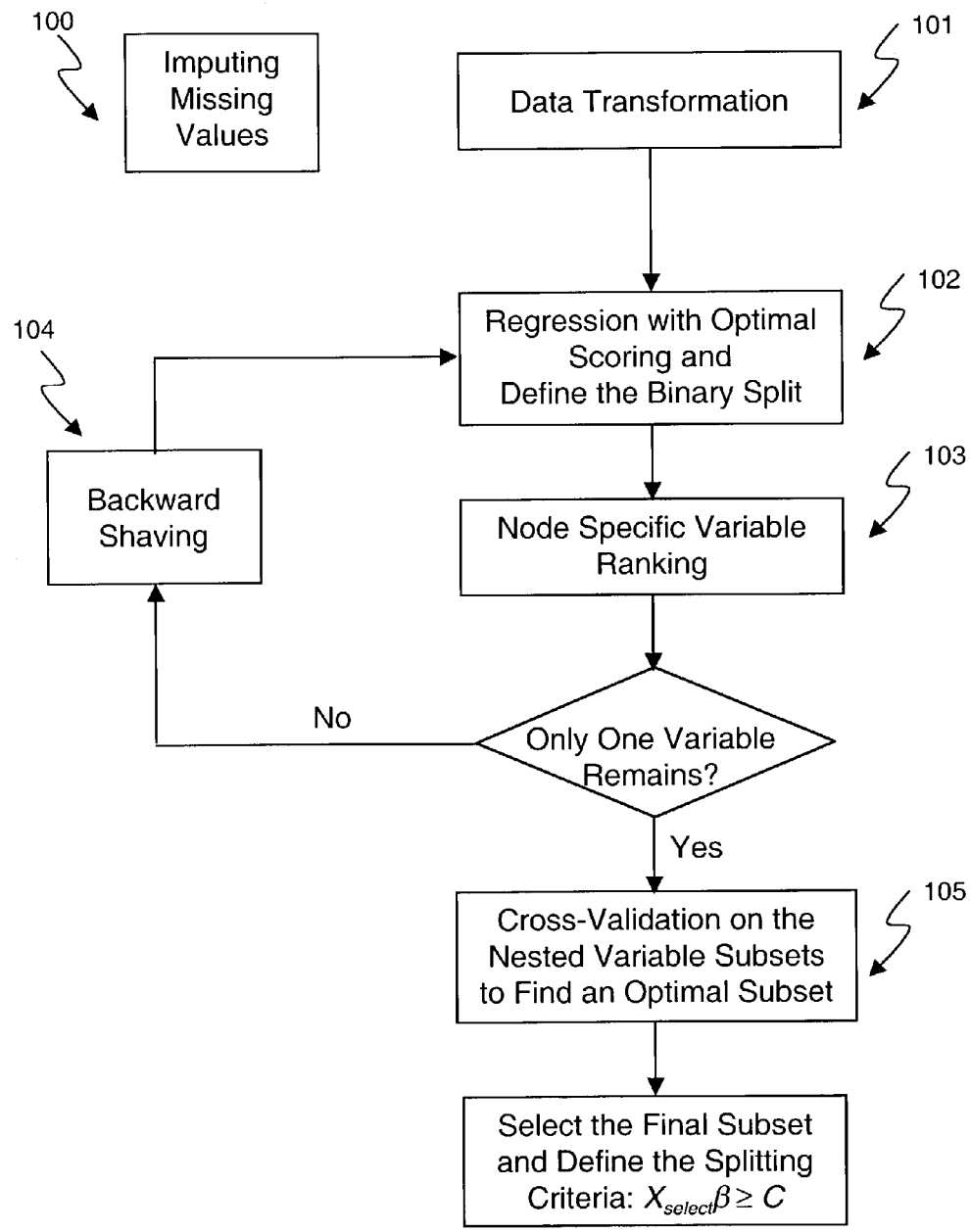
FIG. 1 is a flowchart illustrating the logical steps of the methodology disclosed herein.

As illustrated in FIG. 1, defining the split may involve the following steps:

Step 100: Imputing missing values, when applicable.

Step 101: Coding categorical features into 0–1 dummy variables. The categorical predictors are coded into dummy indicator variables so that they will be amenable to a regression framework. In some genetic situations, a coordinate for the wild type is suppressed for reasons that owe to the rank of the design matrix. This step is skipped when the features (predictors) are quantitative.

Step 102: Applying optimal scoring on the outcome and using the regression framework to define the binary partition criterion. The outcome (class) is coded into a dummy indicator, and the first canonical variables that relate outcome and predictors are computed. This is the solution to a simple eigenvalue problem. Class membership is now transformed to the computed "optimal" score.

Step 103: Applying a statistical test with bootstrapped covariance estimate to calculate node specific variable ranking.

Step 104: Performing backward variable selection based on node specific variable ranking. Backward shaving is necessary to eliminate overfitting. The procedure itself is quite different from standard backward selection used in regression for two main reasons. First, the number of candidate predictors involved is substantial, causing singularity problem. Second, many regression assumptions are violated in different ways, as will be explained hereinafter.

Step 105: Determining the optimal size of the variable subset via cross-validation. K-fold (k=5 or 10) cross-validation is performed on the nested families of predictors produced by backward shaving. It is used to determine the optimal size of the selected variable subset. This procedure is repeated T times, and the mean of the T cross-validated estimates of the reduction in impurity is computed for each set of nested predictors. The set with largest mean reduction (to within the usual 1-SE rule) is selected to finalize the binary split. As one skilled in the art would appreciate, the algorithm can be implemented with any suitable cross-validation technique and is not limited by the particulars disclosed herein. It is anticipated that the robustness of the algorithm can be further enhanced with improvements in procedures thereof such as cross-validation.

These steps will be explained in further details after the following key points:

The "regression with optimal scoring of outcomes" step is the fundamental step of the algorithm. It is used repeatedly in backwards selection of predictors, application of the bootstrap to node-specific variable ranking, and successive cross validation tests to define the optimal subset of predictors. In the final stage, it is applied directly to the selected subset to finalize the binary partitioning criterion.

Regression begins with the full set of predictors and successively shaves off selected proportions of them until only a single predictor remains. This procedure is called "backward shaving." It results in nested families of predictors, from the full set to a single one. The shaving includes two main steps:

1. Based on the node-specific variable ranking defined in what follows, the outcome as transformed is regressed on the coded predictors, successively for subsets of predictors that diminish in size by one, from least significant to most; each subset yields a reduction in the generalized Gini index of diversity.
2. Shave the successively "less important" or "less significant" variables so that the remaining lead to the largest reduction in the generalized Gini index of diversity for the original problem of classification.

A permutation test is applied to determine if there is a "true" association between the selected predictors and outcome beyond noise, i.e., how significant is the split comparing to random noise. A significant (linear) association exists between the outcome and the predictors in the optimal subset when a permutation test statistic is larger than a pre-determined threshold, in which case, the splitting process is repeated with the optimal subset being treated as a full set. The permutation test serves as a subsidiary stopping rule when the splitting is not significant, thereby saving subsequent unnecessary computation.

1. Data Transformation

In the situation of finding influential genes for a polygenic disease, the outcome is a dichotomous disease status: affected versus disease free, and the predictors are mutations at different loci; they are all qualitative, which need to be transformed appropriately.

The response variable $\tilde{Y}$ with $L_0$ unordered classes and N observations is changed into an N by $L_0$ dummy matrix with 0 or 1 elements: $\tilde{Y} \Rightarrow Y_{N \times L_0}$. Each observation is transformed into a $L_0$-dimensional indicator vector:

$$\tilde{y}_n \Rightarrow y_n \quad 1 \leq n \leq N \quad (1)$$

$$y_n = (y_{n1}, y_{n2}, \ldots, y_{nL_0}) \quad y_{nl} = \begin{cases} 1, & \text{if } \tilde{y}_n = c_l \\ 0, & \text{otherwise} \end{cases} \quad 1 \leq l \leq L_0. \quad (2)$$

A predictor with K levels is represented by K–1 instead of K columns in the design matrix to avoid singularity. One level of each variable is chosen as the baseline, and the corresponding column is removed. With J nominal categorical predictors $\tilde{X}_j$, $1 \leq j \leq J$; each having N observations and $L_j$ classes, the design matrix X is $X=(1, X_1, X_2, \ldots, X_J)=X_{N \times (\Sigma L_j - J + 1)} = X_{N \times M}$ where $M=1+\Sigma(L_j-1)=\Sigma L_j - J + 1$.

2. Regression and the Splitting Criteria

The regression framework is built on the transformed data. The outcome is calculated as "optimal" scores, that are the first canonical variables that relate outcome and predictors. The classification problem is thus transformed to a regression one, and the binary splitting rule is defined as an inequality involving a linear combination of a subset of the predictors: $X_{select}\beta \geq C$.

Optimal scoring aims to find a set of scores to assign to the different classes of the outcome so that it can be predicted best by linear combinations of the predictors. It can be viewed as an asymmetric version of canonical correlation analysis and linear discriminant analysis. The optimal scores $\Theta = \Theta_{L_0 \times 1} = (\theta_1, \theta_2, \ldots, \theta_{L_0})'$ are determined as those that minimize the penalized sum of squares $$N^{-1}(\|Y\Theta - X\beta\|^2 + \beta^T \Omega \beta) \quad (3)$$

under the constraint $$\frac{\|Y\Theta\|^2}{N} = 1.$$

$\Omega$ is the penalty term aimed to avoid singularity. When X is not full rank, $\Omega$ will be a small positive diagonal matrix ($\Omega=\lambda I$); otherwise, $\lambda=0$.

For any given score $\Theta$, the penalized least squares estimate of $\beta$ is:

$$\hat{\beta} = (X^T X + \Omega)^{-1} X^T Y \Theta. \quad (4)$$

Substitute $\beta$ with $\hat{\beta}$ (4) in (3); the formula simplifies to:

$$1 - \Theta^T Y'X(X'X+\Omega)^{-1}X'Y\Theta. \quad (5)$$

$\Theta$ that minimizes (5) is the eigenvector corresponding to the largest eigenvalue of matrix:

$$Y'X(X'X+\Omega)^{-1}X'Y. \quad (6)$$

It is standardized to satisfy the constraint $$\frac{\|Y\Theta\|^2}{N} = 1.$$

After the optimal scores are obtained, linear regression of the quantified outcome Z on X is applied:

$$Z = Y\Theta = X\beta + \epsilon. \quad (7)$$

Singularity occurs frequently when there are many predictors involved or in the later stage of the partition, where the sample within a node is relatively homogeneous. To avoid singularity, a ridge regression is employed with penalty term $\Omega=\lambda I$, where $\lambda$ is a small positive number.

$$\|Z-X\beta\|^2 + \beta'\Omega\beta \quad \Omega=\lambda I \quad (8)$$

is minimized, which entails estimated regression coefficients and outcome as $$\hat{\beta} = (X'X+\Omega)^{-1}X'Z = (X'X+\Omega)^{-1}X'Y\Theta \text{ and} \quad (9)$$

$$\hat{Z} = X(X'X+\Omega)^{-1}X'Z = X(X'X+\Omega)^{-1}X'Y\Theta. \quad (10)$$

When X is full rank, simple linear regression is applied:

$$\hat{\beta} = (X'X)^{-1}X'Z = (X'X)^{-1}X'Y\Theta \text{ and} \quad (11)$$

$$\hat{Z} = X(X'X)^{-1}X'Z = X(X'X)^{-1}X'Y\Theta. \quad (12)$$

The binary split is defined as $\hat{Z}=X\hat{\beta} \gtreqless C$. C is chosen to maximize the impurity reduction:

$$\text{optimal split} = \underset{n}{\arg\max} R_t - R_l - R_r \quad (13)$$

where $R_t$ indicates the weighted generalized Gini index for the current node t, $R_l$ is the weighted Gini index for the left daughter node of any given partition; and $R_r$ is the weighted Gini index for the right daughter node.

At this point, one would need to know how to choose the right subset of predictors on which to perform the regression and how to measure the relative importance of each predictor involved. Here, we first introduce a node specific variable ranking based on bootstrap estimates; then we describe a backward selection procedure to choose the variables.

3. Backward Shaving and Node Specific Variable Ranking

"Backward shaving" begins with the full set of predictors and successively shaves off selected proportions of them until only a single predictor remains. This procedure rends nested families of predictors, from the full set to a single one.

The shaving is based on the node-specific variable ranking defined by bootstrapped p-values. Such p-values are derived from a chi-square statistic as it applies to testing the null hypothesis that the vector of bootstrapped regression coefficients has all coordinates zero. Because the observations are often correlated and the predictors categorical, we suggest using a statistic from the bootstrap estimates to evaluate variable importance. The hypothesis being tested is:

$$H_0: \beta_{(X_i)} = (0,0,\ldots,0) \text{ versus } H_a: \beta_{(X_i)} \neq (0,0,\ldots,0) \quad (14)$$

where $\beta_{(X_i)}$ indicates the subset of regression coefficients that represents predictor $X_i$.

The underlying assumption is that $\hat{\beta}_{X_i}$, the least squares estimate of $\beta_{(X_i)}$, has a multi-normal distribution $\hat{\beta}_{(X_i)} \sim N(\mu, \Sigma)$, which implies that the solid ellipsoid of Z values satisfying $$(Z-\mu)'\Sigma^{-1}(Z-\mu) \leq \chi_{l_i}^2(\alpha) \quad (15)$$

has probability $1-\alpha$.

Bootstrap is used to correctly estimate $\mu$ and $\Sigma$. We first bootstrap families to obtain B independent bootstrap samples $(X^{*1}, Y^{*1}), (X^{*2}, Y^{*2}), \ldots, (X^{*B}, Y^{*B})$. For each sample, we estimate the optimal score $\Theta^{*b}$ and the regression coefficients:

$$\hat{\beta}^{*b} = (X^{*b\prime}X^{*b}+\Omega)^{-1}X^{*b\prime}Y^{*b}\Theta^{*b} \; b=1,\ldots,B \quad (16)$$

We then compute the sample mean and sample covariance of $\hat{\beta}_{(X_i)}$ from the B bootstrapped estimates $$\hat{\beta}_{(x_i)}^{*b} b = 1 \text{ to } B:$$

$$\hat{\mu} = \hat{\text{Mean}}(\hat{\beta}_{(x_i)}) = \overline{\hat{\beta}_{(x_i)}^*} = \frac{1}{B}\sum_{b=1}^{B}\hat{\beta}_{(x_i)}^{*b} \quad (17)$$

$$\hat{\Sigma} = \hat{\text{Cov}}(\hat{\beta}_{(x_i)}) = \frac{1}{B-1}\sum_{b=1}^{B}\left(\hat{\beta}_{(x_i)}^{*b} - \overline{\hat{\beta}_{(x_i)}^*}\right)'\left(\hat{\beta}_{(x_i)}^{*b} - \overline{\hat{\beta}_{(x_i)}^*}\right) \quad (18)$$

With the bootstrap estimates $\hat{\mu}$ and $\hat{\Sigma}$, the test statistic is built as:

$$X^2 = (\hat{\mu}-0)'\hat{\Sigma}^{-1}(\hat{\mu}-0) = \hat{\mu}'\hat{\Sigma}^{-1}\hat{\mu} \quad (19)$$

which has approximately a multinormal $\chi_{l_i}^2$ distribution under the multi-normal assumption, where $l_i$ is the number of columns used in the design matrix to represent variable $X_i$. The p-value derived from this test statistic corresponds to the $(1-p)$ % ellipsoid-confidence-contour, where the boundary goes through the origin.

These p-values not only give a measure of the variable importance, but also provide an order for shaving. We repeatedly shave off a certain number of "least important" or "least significant" variables until only one variable left, creating a nested sequence of variable subsets, where the first subset $S^{(1)}$ includes the single most important or significant variable. The last set $S^{(m)}$ includes all the current candidate variables:

$$S_{full\;set} = S^{(m)} \supset S^{(m-1)} \supset \ldots \supset S^{(2)} \supset S^{(1)}. \quad (20)$$

The subset $S_1 = S^{(i_1)}$ that includes the least number of variables yet achieves approximately the largest impurity reduction within a pre-specified error margin is chosen. In this example, the error margin is set to be 5% of the largest impurity reduction.

$$i_1 = \min_i\{i \mid G(S^{(i)}) \geq [\max_{1 \leq j \leq m} G(S^{(j)}) - \text{error margin}]\} \quad (21)$$

Variables that are not included in $S_1$ are shaved off. In the case where $S_1 = S^{(m)}$, one variable with the least significant p-value will be shaved off and the process continues.

Next, $S_1$ is treated as the full set and the shaving procedure is repeated on $S_1$ to get an even smaller set. Again, this shaving procedure continues until only one variable left. As a result, a sequence of nested variable subsets is produced:

$$\text{full set} = S_0 \supset S_1 \supset S_2 \supset \ldots \supset S_{h-1} \supset S_h = \text{a single variable}.$$

It is important to note that the shaving technique disclosed herein shaves off predictors that are the least important or the least significant in defining a specific binary split. This is principally different from shaving techniques that shave off observations that are the least similar to the leading principal component of (a subset of) the design matrix.

The optimal subset is determined by the mean of the cross-validated estimates. K-fold cross-validation (k =5 or 10) is applied on each set in the nested sequence to estimate the impurity reduction associated with the subset:

$$\Delta R^{cv}(S_i) = R_t - R_{tl}^{cv}(S_i) - R_{tr}^{cv}(S_i), \quad (22)$$

where $R_t$ is the impurity measure of the current node t according to the cross-validated partition rule, using variable subset $S_i$; $R_{tl}^{cv}(S_i)$ is the impurity measure of the left daughter node ; $R_{tr}^{cv}(S_i)$ is the impurity measure of the right daughter node. Since single cross-validation is relatively unstable, it is repeated M=40 times, each time with a different k-nary partition of the data. The means of the M cross-validated estimates represents the performance of each subset:

$$\overline{\Delta R}^{cv}(S_i) = \frac{1}{M}\sum_{m=1}^{M} R_m^{cv}(S_i). \quad (23)$$

The subset with the largest mean within 1-SE rule is chosen as the final variable subset to define the binary split.

After the final set is chosen, a permutation test is performed to test whether there is any (linear) association between the outcome and the predictors in $S_i^*$. If the test statistic is larger than a pre-determined threshold, we conclude there is still significant association between the chosen predictors and the outcome and continue splitting the node. Otherwise, we stop. In a sense, it serves as a subsidiary stopping rule.

4. Missing Value Imputation

Some data, e.g., genetic information, are prone to missing value problems. Retaining observations with missing values can avoid losing valuable information therein. In the case of genetic data, since they (predictors) are often moderately or highly correlated, such correlation can be used to establish a predictive model for those with missing values, using all other predictors. For the purpose of this disclosure, the standard classification-tree method, known as CART®, is selected to serve as a predictive model for two main reasons. First, it is flexible: applicable to both categorical and continuous variables without making any distribution assumptions. Second, it deals with missing values effectively through surrogate splits and succeeds in the situation where many predictors in the training set have missing parts.

Observations with missing value on the targeted variable are grouped as a test set, while the others form the learning set. The learning set is then used to grow a standard classification tree, with the target variable serving as the outcome. The test set is then fitted into this classification tree giving a prediction to each originally missing value. Such an imputation scheme is valid to the extent that data are missing at random. Here, "valid" means the imputation procedure does not distort the real model or the predicted values in any way. "Missing at random" means the causes of the data being missing are independent of any observed values.

Working Examples

The methodology can be used in any situation in which a dataset is given with predictors and outcome (missing values are allowed in predictors, but not in the outcomes). It can be used for supervised learning on general or complex datasets. It is generally applicable to any complex datasets where multiple factors (predictors) determine an outcome and particularly applicable to assessing gene by gene interactions and gene by environment interactions related to complex diseases. Described below are examples of the above-described methodology and algorithm as applied to simulated and real-world complex datasets.

1. Simulations

Two groups of datasets are used in the simulations: one representing the cumulative effects and the other interactive effects. In this exemplary embodiment, they illustrate two possible pathways by which candidate genes work together to determine polygenic disease status. In the former case (cumulative effects), the contribution from each gene is small but their effects can accumulate over some threshold, thus changing a person's risk of disease. In the latter case (interactive effects), a person would need mutations at several specific genes simultaneously to change risk status.

Genetic mutations could be presented in many ways. In this example, we focus on SNPs (single-nucleotide polymorphisms). SNPs are changes of nucleotides at a single locus of DNA. Nucleotide is the basic structural unit of DNA. There are about three billion nucleotide base pairs that make up the human genetic code. SNPs are the most common genetic variations and occur approximately once every 100 to 300 bases. They can be disease mutations themselves. They may be located close to the disease genes and serve as markers. Multiple mutations at one locus do exist. However, the most common mutation is a single change from the wild type to a specific mutant type. Since humans have two DNA strands, under the "single change" assumption, there will be three genotypes at each locus. Using "1" to denote the wild-type and "2" to denote the mutant type, the three genotypes are:

1. "1/1"—no mutation at either DNA strand.
2. "1/2" or "2/1"—a mutation at one DNA strand but not the other. Since which DNA strand has the mutation does not make a difference in the genetic effect, these two genotypes are treated as the same in this example.
3. "2/2"—mutations on both DNA strands.

SNPs that have three different levels at each locus are an example of categorical variable. The goal here is to reveal correctly the complicated interactive structures among various gene mutations and find the influential combinations of SNPs that have high predictive power on disease status.

1.1 Cumulative Effects

In this simulation, 200 samples are generated, each with complete SNP information on 30 loci, namely "locus 1" to "locus 30". The SNPs at each loci are independent and follow the Hardy-Weinburg law with the probabilities: P("1/1")=P("2/2")=0.25 and P("1/2" or "2/1")=0.5.

The SNPs on the first 6 loci, namely "locus 1" to "locus 6", determine each observation's disease status; and the remaining 24 SNPs are simply noise. Denote the number of mutations on the first 6 loci by M (i.e., the number of "2"s among the genotypes at the first six loci). The distribution of the disease status conditioning on the genotypes at the first six loci is listed in Table 1.

TABLE 1

| Genotype: G | P (Disease \| G) | P (Disease Free \| G) |
|---|---|---|
| 0 ≤ M < 4 | 0.0 | 1.0 |
| 4 ≤ M < 6 | 0.1 | 0.9 |
| 6 ≤ M < 7 | 0.5 | 0.5 |
| 7 ≤ M < 9 | 0.9 | 0.1 |
| 9 ≤ M < 12 | 1.0 | 0.0 |

The conditional probabilities show that the more mutations a person has in the first 6 loci, the more likely she/he is going to have the disease. People do not have to have mutations at any specific gene to get the disease. As long as they accumulate enough mutations among the first six genes, they will fall into a relatively high risk group. Overall, about half the observations have the disease, and the remaining are disease-free. In this specific example, there are 89 diseased and 111 disease free observations. This simulation illustrates the case where the cumulative effects of several genes determine the outcome. That is, these genes are individually insignificant. Together they produce a predominant effect.

Figure 2:
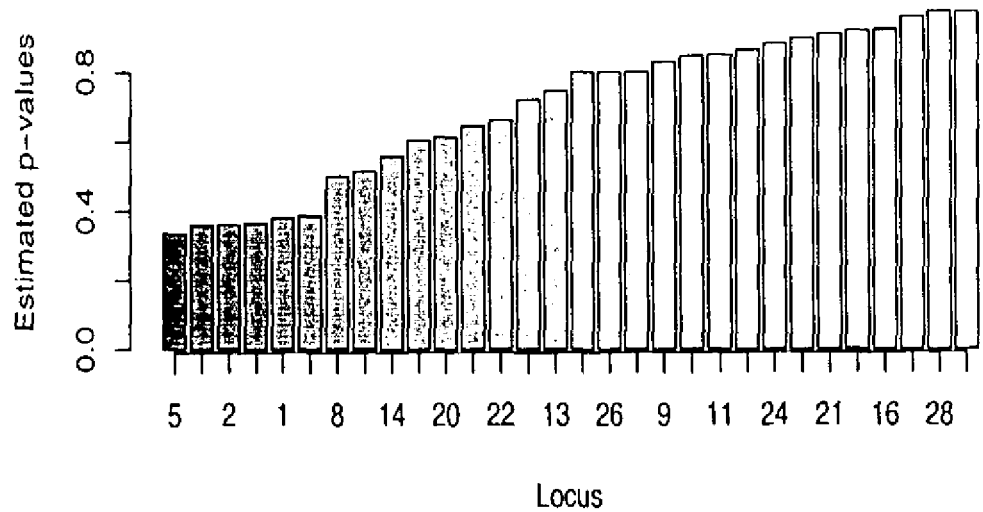
FIG. 2 shows the backward shaving step of FIG. 1 with cumulative effect.
Figure 2:
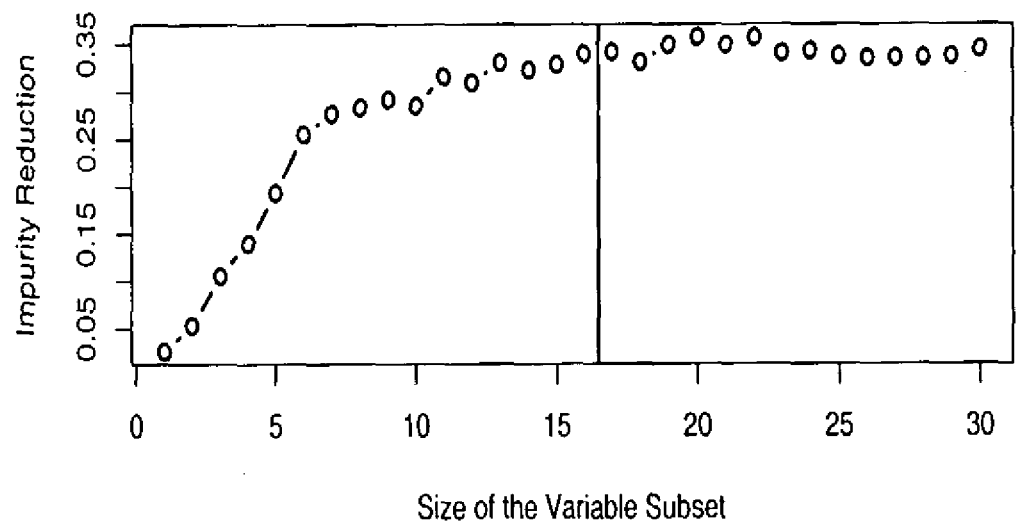
Figure 3:
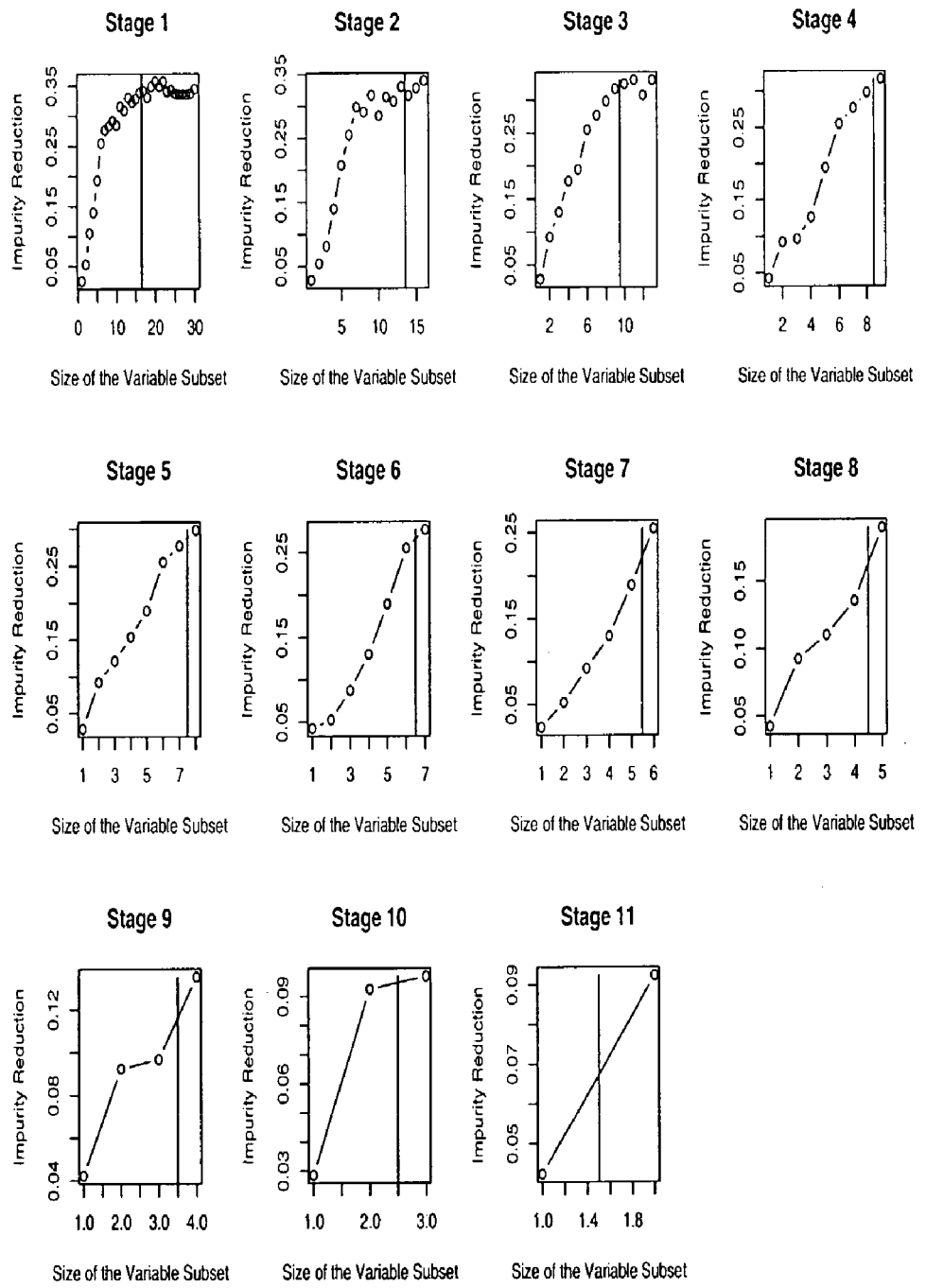
FIG. 3 illustrates the backward shaving step of FIG. 2 in stages.

FIGS. 2 and 3 show how backward shaving works. FIG. 2 illustrates the initial step of the backward shaving, where initially all SNPs were on 30 loci. The upper part of the figure shows the variables ranked according to their relative importance (estimated p-values). The x-axis indicates the SNP locus corresponding to each bar. The lower part of the figure shows the impurity reduction caused by a binary partition using a particular variable subset: the left most point indicates the impurity reduction caused by using the variable with the smallest p-value (the one with the lowest bar on the upper part of the figure); the second left most point indicates the impurity reduction caused by using the variables with the smallest and the second smallest p-values, and so on; the right most points is the reduction caused by using all 30 variables. The shave-off point is where the impurity reduction is very close to the maximum, yet only a relatively small number of variables are involved. In this case, the first shave off point is after the 16$^{th}$ most important variable.

This procedure continues on the remaining 16 variables, and is repeated until only one variable left. In this example, the backward shaving produces a nested sequence of variable subsets, as shown in Table 2 below and in FIG. 3.

TABLE 2

| Variable Subset | Loci Included |
|---|---|
| 1 | All 30 variables |
| 2 | 1 2 3 4 5 6 8 12 13 14 15 17 18 19 20 22 |
| 3 | 1 2 3 4 5 6 8 14 15 17 19 20 22 |
| 4 | 1 2 3 4 5 6 8 14 19 |
| 5 | 1 2 3 4 5 6 8 19 |
| 6 | 1 2 3 4 5 6 8 |
| 7 | 1 2 3 4 5 6 |
| 8 | 1 3 4 5 6 |
| 9 | 1 3 5 6 |
| 10 | 1 3 6 |
| 11 | 1 6 |
| 12 | 1 |

Figure 4:
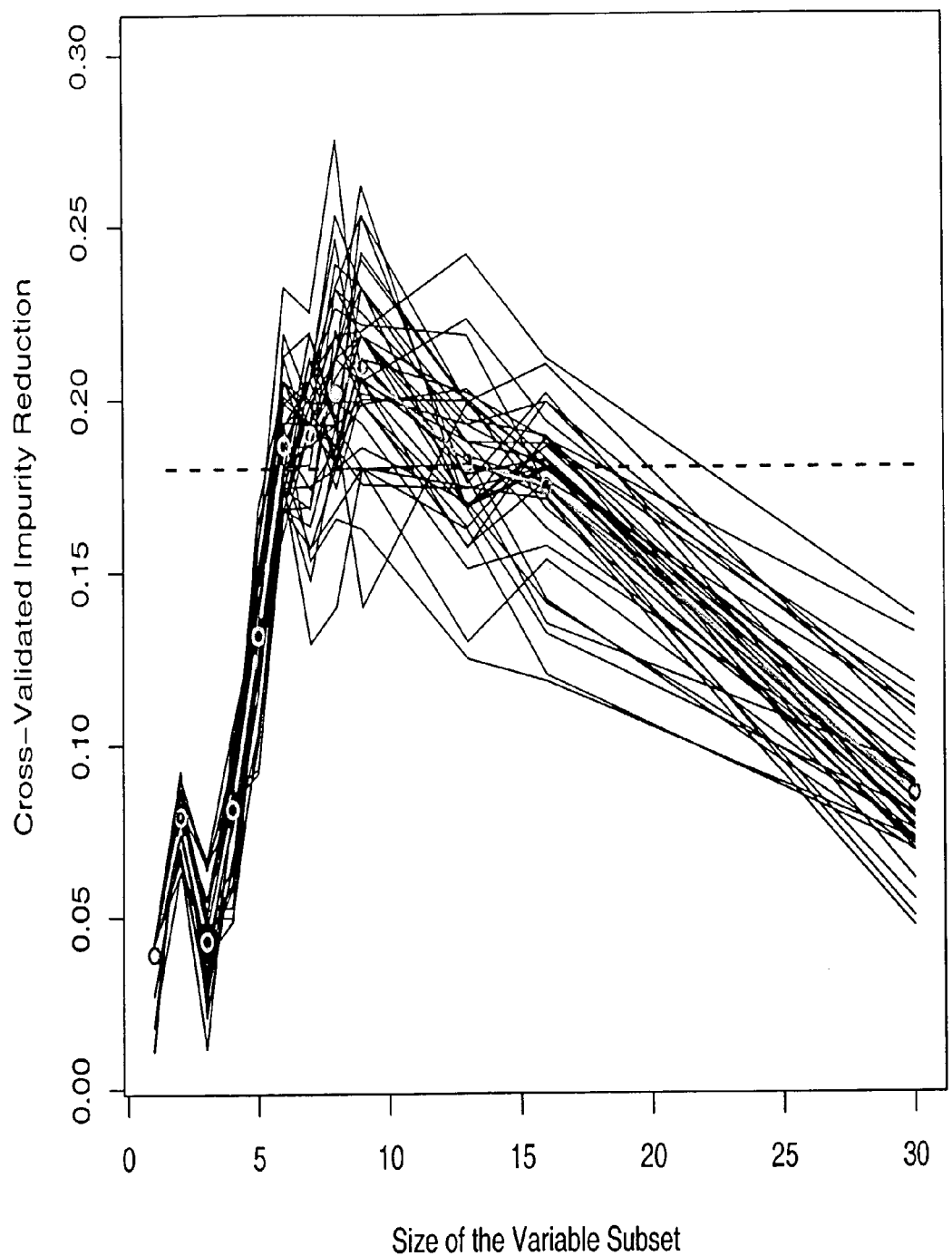
FIG. 4 demonstrates the cross-validation step of FIG. 1 with cumulative effect.

Cross-validation is performed T=40 times on these 12 nested variable subsets. The variable subset with the largest mean of the T=40 cross-validated estimates within a 1-SE rule is selected. This procedure is illustrated in FIG. 4 where each thin solid line represents one cross-validation. The thick broken line is the mean of all 40 cross-validations. The dashed horizontal line is the largest mean minus one standard deviation. The selected subset is: SNPs at loci 1 to 6, which is exactly the set of all six influential gene mutations.

The optimal scores assigned to the outcome are listed in Table 3.

TABLE 3

| Disease Status | Score |
|---|---|
| Diseased | 1.156 |
| Disease Free | 0.763 |

The partition criterion: $X\hat{\beta} \geq C$ is:

0.498 + 0.119 Locus 1:1/2 + 0.144 Locus 1:2/2 + 0.093 Locus 2:1/2 +

0.183 Locus 2:2/2 + 0.057 Locus 3:1/2 + 0.135 Locus 3:2/2 +

0.087 Locus 4:1/2 + 0.152 Locus 4:2/2 + 0.071 Locus 5:1/2 +

0.151 Locus 5:2/2 + 0.065 Locus 6:1/2 + 0.155 Locus 6:2/2 > 0.979.

Table 3 shows that diseased people have high outcome score (1.156) while disease-free people have low score (0.763). In the partition criterion, all the regression coefficients are positive and draw the predicted value toward the direction of the high disease-outcome score. These consistently positive coefficients correctly identify gene mutations "1/2" or "2/2" on loci 1 to 6 as risk factors. The regression coefficient for mutation "2/2" at any given locus is always about twice the coefficient value of the corresponding "1/2" mutation, which means that having mutations on both DNA strands (genotype "2/2") has approximately twice the effect on increasing the disease risk than having a mutation on only one strand (genotype "1/2"). This accurately reveals the underlying structure of the simulation.

Table 4 below shows the relative importance of the selected variables: SNPs on loci 1 to 6.

TABLE 4

| Variable (Loci) | 4 | 1 | 3 | 5 | 6 | 2 |
|---|---|---|---|---|---|---|
| p-value | 0.234 | 0.237 | 0.249 | 0.250 | 0.254 | 0.283 |

The relative importance of each variable is very close, and none is statistically significant. Both characteristics are consistent with the cumulative model. Mutation at each locus only contributes a small effect of roughly equal magnitude. Viewed individually, none of the effects is decisive or significant.

These insignificant p-values also show an advantage of our approach. By using backward shaving and cross-validation to define the optimal variable subset, individually insignificant variables are allowed to be included and to form decisive combinations. By contrast, most other variable selection procedures remove variables according to some estimate of their individual predictive powers; if that were the case, some or all of the six influential variables included here would be removed, and no underlying structure could be revealed correctly.

Figure 5:
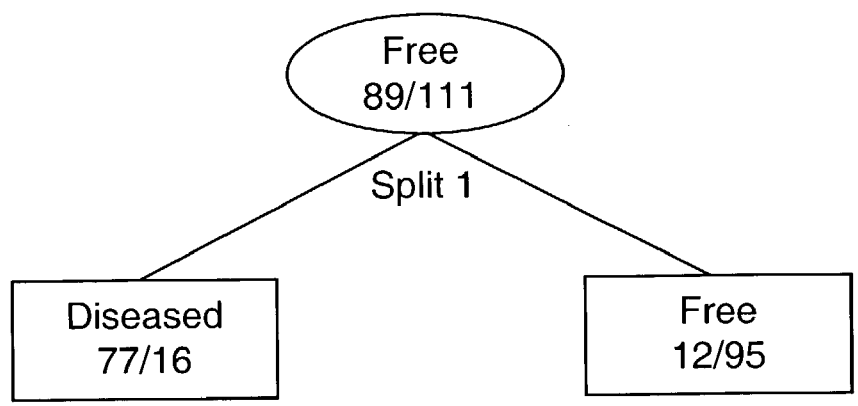
FIG. 5 exemplifies an optimal tree model of FIG. 1 with cumulative effect.

The root partition divides the sample of 200 into two subsets. Further cross-validation and optimal pruning show that this "stump" tree is the optimal model. In other words, with a single split, the optimal model captures the exact six influential variables and the right mechanism of the cumulative effects. FIG. 5 shows estimates of parameters that summarize the "stump", as well as the tree itself. In FIG. 5, sensitivity=77/89=0.865 and specificity=95/111=0.856.

1.2 Interactive Effects

This simulation represents another situation: interactive effects. It is also called epistasis in genetic studies. "Interactive" means that an observation has to have specific genotypes at several influential genes simultaneously to fall into the high risk group.

Same as the cumulative effects simulation, in this simulation, 200 samples are generated, each with complete SNP information on 30 loci; the SNPs on the first 6 loci, namely "locus 1" through "locus 6", determine each observation's disease status. The remaining 24 SNPs are simply noise. However, the mechanism of these genetic effects is different from the first one. The distribution of the disease status conditioned on the genotypes at the first six loci is listed in Table 5.

TABLE 5

| Genotype: G | P (Disease | G) | P (Disease Free | G) |
|---|---|---|
| "2/2" on Locus 1 to 6 | 0.9 | 0.1 |
| Otherwise | 0.1 | 0.9 |

In other words, people with "2/2" mutations on all the first six loci are most likely to get the disease. The rest have a much smaller probability.

The distribution of SNPs at each locus is of independent features. They follow the Hardy-Weinburg law. However, in order to generate a big enough proportion of disease cases, for the first six loci, we assign $P(\text{"2"})=0.9$, so $P(\text{"2/2"})=0.9^2=0.81$;

$P(\text{"1/1"})=(1-0.9)^2=0.01$; and $P(\text{"1/2"})=2\times 0.9\times 0.1=0.18$.

For the remaining 24, $P(\text{"1"})=P(\text{"2"})=0.5$, so $P(\text{"1/1"})=P(\text{"2/2"})=0.25$; and $P(\text{"1/2" or "2/1 "})=0.5$.

In total, there are about $0.81^6\times 0.9+(1-0.81^6)\times 0.1=32.6\%$ diseased people. In the specific set of this simulated sample, there are 68 (34%) diseased people and 132 (66%) disease-free people.

Figure 6:
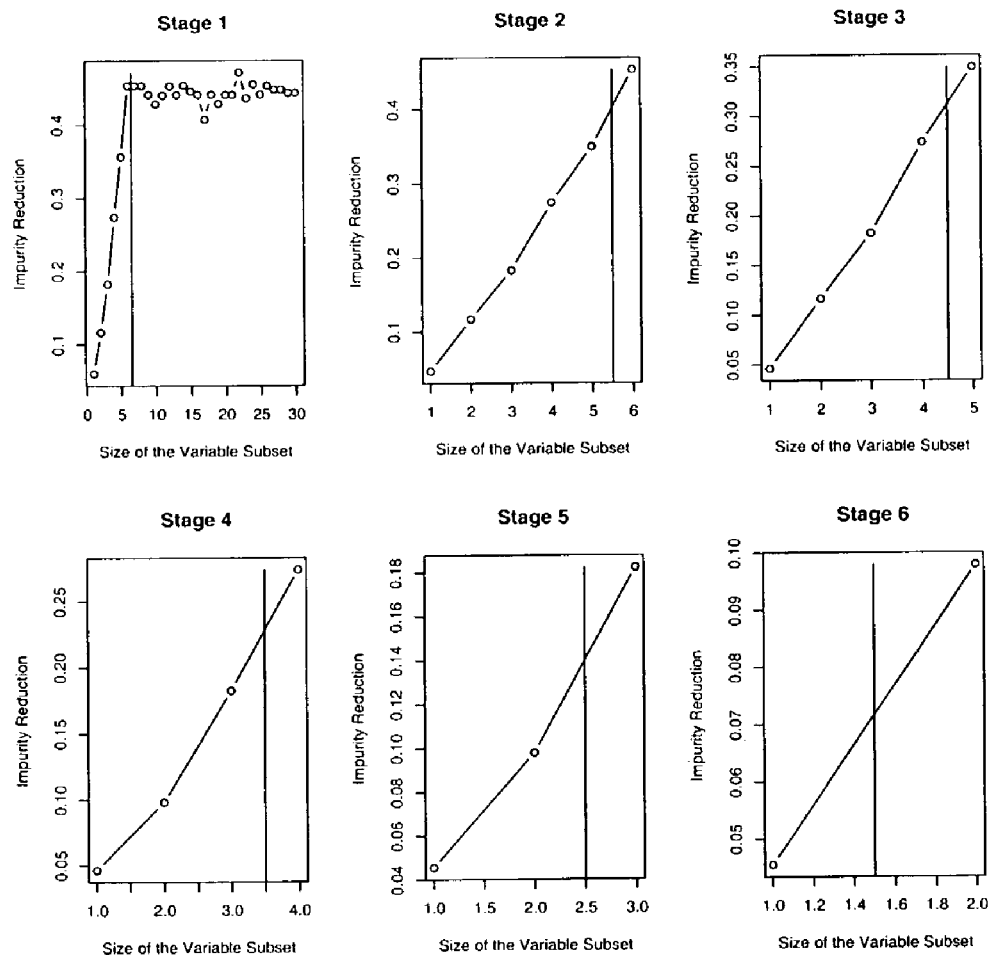
FIG. 6 shows the backward shaving step of FIG. 1 in stages with interactive effect.

The backward shaving goes more quickly here than it does in the cumulative effect situation in which 11 steps were taken, as shown in FIG. 3. Here, shaving from 30 variables to 1 variable took only 6 iterative steps, as shown in FIG. 6. In fact, the first step shaves off the 24 noise variables and gives us the perfect set, as illustrated by the nested sequence of seven variable subsets listed in Table 6.

TABLE 6

| Variable Subset | Loci Included |
|---|---|
| 1 | All 30 variables |
| 2 | 1 2 3 4 5 6 |
| 3 | 1 3 4 5 6 |
| 4 | 3 4 5 6 |
| 5 | 3 5 6 |
| 6 | 3 6 |
| 7 | 3 |

Figure 7:
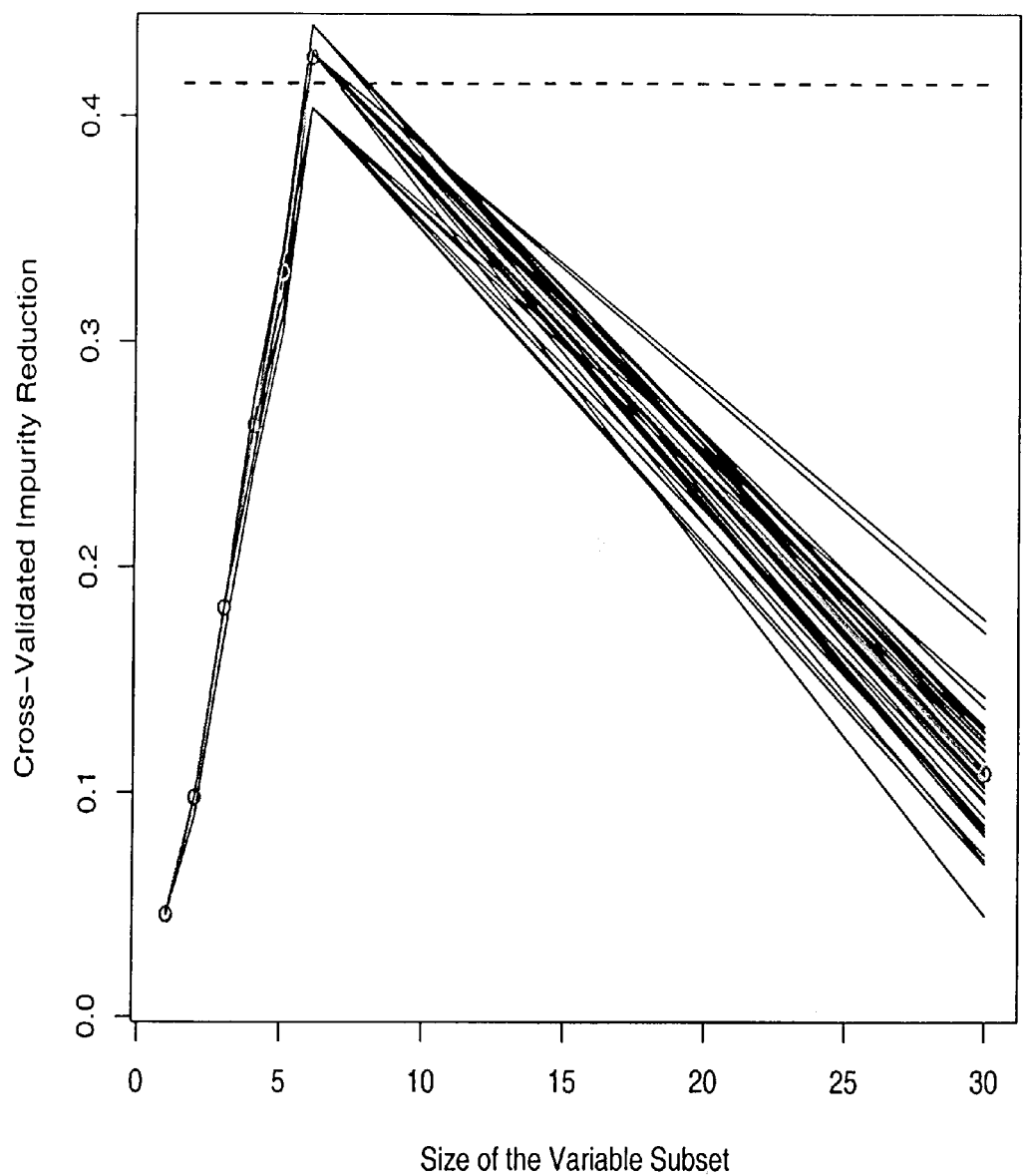
FIG. 7 demonstrates the cross-validation step of FIG. 1 with interactive effect.

The cross-validation performance of each variable subset is shown in FIG. 7. Again, each thin solid line represents one cross-validation estimate. The thick broken line is the mean of the estimates. The dashed horizontal line is the maximum mean minus one standard deviation of the 40 cross-validation estimates at the same point. The smallest subset that reaches the maximal mean of the T=40 cross-validated estimates within 1-SE rule is exactly the subset that includes the first six loci.

The optimal scores assigned to the outcome are listed in Table 7.

TABLE 7

| Disease Status | Score |
|---|---|
| Diseased | 0.423 |
| Disease Free | 1.193 |

The partition criterion: $X\hat{\beta}<C$ is:

$0.779 - 0.305$ Locus $1:1/2 - 0.544$ Locus $1:2/2 + 0.284$ Locus $2:1/2 +$ $0.024$ Locus $2:2/2 + 0.516$ Locus $3:1/2 + 0.263$ Locus $3:2/2 +$ $0.253$ Locus $4:1/2 - 0.033$ Locus $4:2/2 + 0.045$ Locus $5:1/2 -$ $0.286$ Locus $5:2/2 + 0.727$ Locus $6:1/2 + 0.445$ Locus $6:2/2 < 0.664$.

This time, the linear inequality does not reveal the structure as clearly and directly as in the case of a cumulative effect. However, it still represents accurately the underlying mechanism. In this interactive-effect (epistatic) situation, people in the high risk group must have "2/2" mutations at all of the first six loci, with one or more "1/2" mutations in any of the first six loci, a subject falls into the low risk group. This implies that for the first six loci, while mutation "2/2" is obviously a strong risk factor, mutation "1/2" is a protective factor. Notice that diseased people have lower outcome score (0.423) than do the disease-free people (1.193); if this is correct, then for any given locus (1 to 6), the regression coefficient for the "1/2" genotype (the protective factor) should be consistently and substantially larger than the coefficient for the "2/2" genotype (the risk factor), which is exactly the case in the linear inequality. On the other hand, the seemingly random signs of the regression coefficients do not imply an incorrect model. Due to random variation, in some loci, the protective effect of the "1/2" genotype predominates, leading the coefficients of the whole locus to the positive direction, while in some other cases, the risk effect of the "2/2" genotype is more significant, leading the coefficients in the negative direction.

The relative importance of the six variables (node-specific variable ranking) is listed in Table 8.

TABLE 8

| Variable (Loci) | 6 | 5 | 4 | 3 | 1 | 2 |
|---|---|---|---|---|---|---|
| p-value | 1.858e−7 | 2.742e−6 | 1.877e−5 | 2.958e−5 | 2.524e−3 | 1.064e−3 |

This time, the individual significance of each variable is much stronger than the ones in the cumulative-effect model. This is because in the cumulative-effect situation, a person only needs to accumulate enough mutations among the first six loci to fall into the high risk group and does not need to possess any particular mutation. Therefore, each gene's individual effect is small. On the contrary, in the interactive-effect (epistatic) situation, a person has to have homozygous mutations on all six disease genes to fall into the high risk group. Therefore, each gene plays a crucially important role. Such difference is revealed by the magnitudes of the p-values. In the cumulative case, the p-values are all about 0.2. No one is significant. In the interactive case, the p-value for each disease gene is extremely significant.

Figure 8:
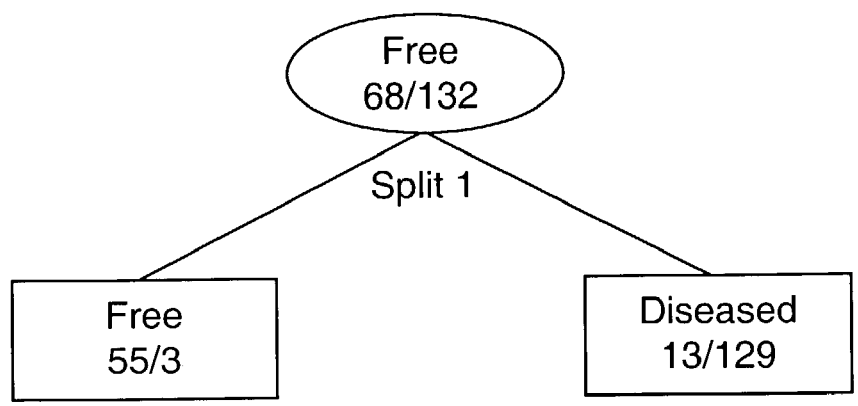
FIG. 8 exemplifies an optimal tree model of FIG. 1 with interactive effect.

Once again, cross-validation and optimal pruning confirm that the root split is the best model. FIG. 8 shows the "stump" tree, with sensitivity=$^{55}/_{68}$=0.8088 and specificity = $^{129}/_{132}$=0.977.

2. SAPPHIRe Project

SAPPHIRe stands for Stanford Asian Pacific Program for Hypertension and Insulin Resistance. Its main goal is to find genes that predispose people to hypertension. Hypertension is a common multi-factorial disease that affects 15 to 20% of the adult population in most Western cultures, and it is one of the major risk factors for stroke, coronary heart disease, and renal failure. It is determined by an individual's genetic make-up and environment. Many twin, adoption, and familial aggregation studies indicate that hypertension is at least in part genetically determined. It is also well known that the most common form of hypertension is polygenic. Because of the complicated mechanism of polygenic disease, and despite intense effort, the main causes of hypertension and its pathogenesis remain largely unknown.

In an effort to identify important gene mutations that predispose people to hypertension, the classification and prediction methodology disclosed herein was applied to SAPPHIRe data that were drawn from three field centers: Stanford, Hawaii, and Taiwan. The sample consists of "affected" sib-pairs. The study design incorporates both concordant sib-pairs (both siblings with hypertension) and discordant sib-pairs (one sib with hypertension and the other with hypotension), though the proband is always hypertensive. In addition, for sib pairs meeting the entry criteria, additional siblings meeting the same criteria (either hypertensive or hypotensive) are also included. The project is an association study focusing on discordant sib pairs to map loci for the quantitative trait. This can be more efficient than the traditional genetic linkage analysis. It can reduce the genotyping by 10 to 40 fold yet still achieves substantial power, although with a possible increase in bias.

Individual based questionnaires were used to obtain information about behavior and environmental risk factors, such as smoking history, alcohol drinking history, education level, etc. The family structure and history of hypertension were obtained by interview with one representative of each family. Medical records, screening tests, and clinical exams were used to collect information such as systolic and diastolic blood pressures; height, weight and BMI; triglycerides, LDL cholesterol, VLDL cholesterol, TC/HDL ratio and other information about blood lipids. Genetic information was obtained by using fluorogenic probes (TaqMan, Perkin Elmer). Genotyping with single-nucleotide polymorphisms can be automated easily and can allow researchers to do both genome-wide linkage studies with anonymous bi-allelic markers and association studies with candidate genes.

Two datasets from the SAPPHIRe project were used. One small dataset includes 292 women with complete information about SNPs on 22 loci, menopausal status, insulin resistance status, and ethnicity. One large dataset includes 850 women with some information about SNPs on 43 different loci, menopausal status, insulin resistance status, and ethnicity. Since there are many missing values on the larger dataset, the dataset is pre-processed using the imputation technique described heretofore.

2.1 Result on Dataset with Complete Information

Table 9 shows the distribution of ethnicity, menopausal status, insulin resistance status, and blood pressure status of the 292 women with complete information.

TABLE 9

| Blood Pressure Status | Hypertensive: 197 | Hypotensive: 95 |
| Ethnicity | Chinese: 231 | Japanese: 61 |
| Menopausal Status | Menopaused: 167 | Pre-menopaused: 125 |
| Insulin Resistance Status | Resistant: 102 | Non-resistant: 190 |

The number of hypertensive cases is about twice the number of hypotensive cases, and this suggests a 1:2 ratio of costs. That is, misclassifying a hypotensive case costs twice as much as misclassifying a hypertensive case. Also, giving blood pressure lowering medications to an individual already hypotensive might have unfortunate outcome.

Figure 9:
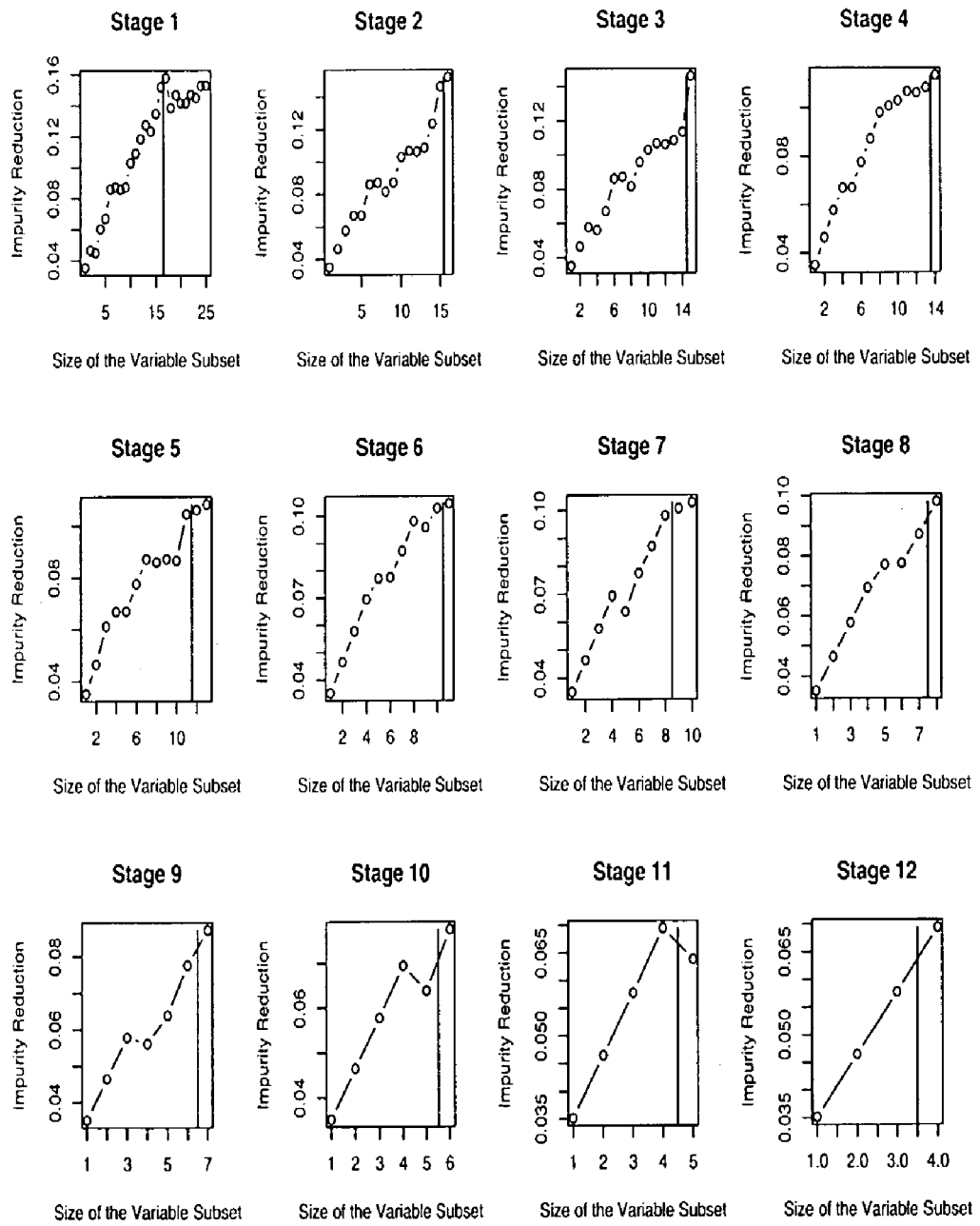
FIG. 9 shows the backward shaving step of FIG. 1 with SAPPHIRe data.

The root split starts with the 292 observations and all 25 predictors (22 SNPs, insulin resistance status, menopausal status, and ethnicity). The backward shaving procedure generates 15 nested variable subsets. FIG. 9 shows the first 12 of the 15 stages of the shaving procedure. Table 10 lists the 15 nested variable subsets.

TABLE 10

| Number | Variables Included |
|---|---|
| 1 | All 25 predictors |
| 2 | AGTG6A, HUT2SNP1, HUT2SNP2, HUT2SNP3, HUT2SNP5, BADC47T, MLRx6, CD36, PTP, AVPR2A1629G, AGT2R2C1333T, PPARG12, ACE, Ethnicity, Menopausal Status, Insulin Resistance Status |
| 3 | AGTG6A, HUT2SNP1, HUT2SNP2, HUT2SNP3, HUT2SNP5, BADC47T, CD36, PTP, AVPR2A1629G, AGT2R2C1333T, PPARG12, ACE, Ethnicity, Menopausal Status, Insulin Resistance Status |
| 4 | AGTG6A, HUT2SNP1, HUT2SNP2, HUT2SNP3, HUT2SNP5, CD36, PTP, AVPR2A1629G, AGT2R2C1333T, PPARG12, ACE, Ethnicity, Menopausal Status, Insulin Resistance Status |
| 5 | AGTG6A, HUT2SNP1, HUT2SNP2, HUT2SNP3, HUT2SNP5, CD36, PTP, AGT2R2C1333T, PPARG12, ACE, Ethnicity, Menopausal Status, Insulin Resistance Status |
| 6 | HUT2SNP1, HUT2SNP2, HUT2SNP3, HUT2SNP5, CD36, PTP, PPARG12, ACE, Ethnicity, Menopausal Status, Insulin Resistance Status |
| 7 | HUT2SNP1, HUT2SNP2, HUT2SNP3, CD36, PTP, PPARG12, ACE, Ethnicity, Menopausal Status, Insulin Resistance Status |
| 8 | HUT2SNP3, CD36, PTP, PPARG12, ACE, Ethnicity, Menopausal Status, Insulin Resistance Status |

TABLE 10-continued

| Number | Variables Included |
|---|---|
| 9 | HUT2SNP3, CD36, PTP, PPARG12, Ethnicity, Menopausal Status, Insulin Resistance Status |
| 10 | CD36, PTP, PPARG12, Ethnicity, Menopausal Status, Insulin Resistance Status |
| 11 | PTP, PPARG12, Ethnicity, Menopausal Status, Insulin Resistance Status |
| 12 | PPARG12, Ethnicity, Menopausal Status, Insulin Resistance Status |
| 13 | Ethnicity, Menopausal Status, Insulin Resistance Status |
| 14 | Ethnicity, Insulin Resistance Status |
| 15 | Ethnicity |

Figure 10:
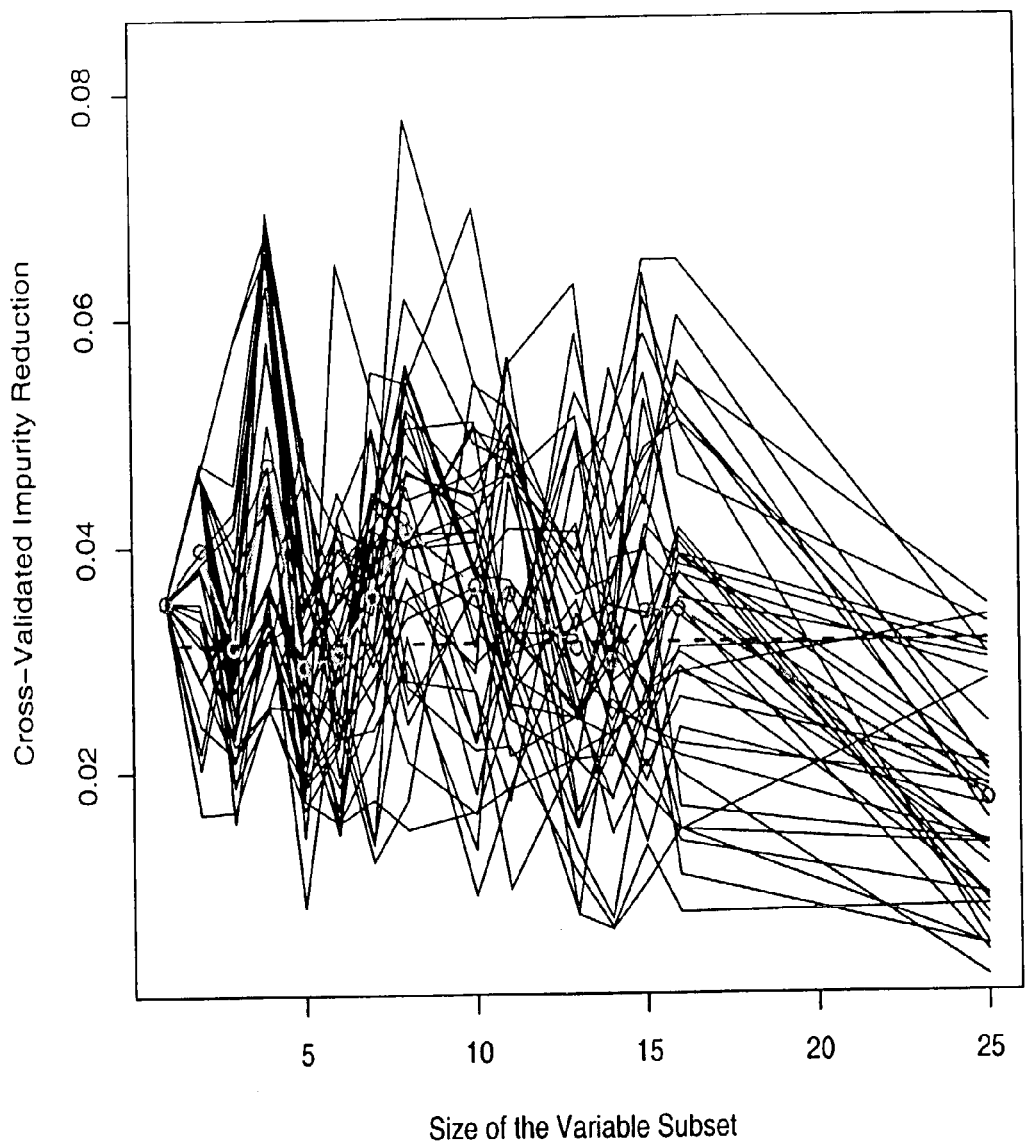
FIG. 10 demonstrates the cross-validation step of FIG. 1 with SAPPHIRe data.

The cross-validated performance of each variable subset is shown in FIG. 10. The thin solid lines are the impurity estimates of one cross-validation. The thick broken line is the mean of the T=40 cross-validated estimates. The dashed horizontal line is the maximum mean minus the standard deviation. Notice the standard deviations are high across all the 15 variable subsets. The smallest subset that reaches the maximal mean of the T=40 cross-validated estimates (within 1-SE) is the subset that includes only one variable: Ethnicity. The significance of the Ethnicity variable has p-value<0.00001 and the permutation t-statistic is t=10.4871.

This split groups the Japanese people to the right and the Chinese people to the left. It is therefore obvious that the blood pressure status is substantially different across the two ethnic groups. Such difference, of course, is related to how subjects were recruited in the first place. The subjects in Hawaii are mainly Japanese with dominant proportion of hypertensive cases. On the other hand, the subjects in Taiwan are all Chinese, and the subjects in Stanford are mostly Chinese; and the percentage of hypotensive cases is much higher in both places. Table 12 shows such extreme distributions, the number on the left of "/" indicates the hypertensive cases, while the number on the right indicates hypotensive cases.

TABLE 12

| | Stanford | Hawaii | Taiwan |
|---|---|---|---|
| Japanese | 8/3 | 46/4 | 0/0 |
| Chinese | 22/13 | 7/0 | 114/75 |

The chi-square ($\chi^2$) test on association between ethnicity and blood pressure status confirms such differences, as shown in Table 13. The odds ratio estimate (OR) shows that being a Japanese rather than a Chinese increases the risk of hypertension by almost five fold. This test is a crude estimate without considering the complicated family structure, and it tends to be more anti-conservative.

TABLE 13

| | Japanese | Chinese |
|---|---|---|
| Hypertensive | 54 | 143 |
| Hypotensive | 7 | 88 |

$X^2 = 14.39$ (p < 0.001) OR = 4.747, 95% CI (2.068, 10.896)

Figure 11:
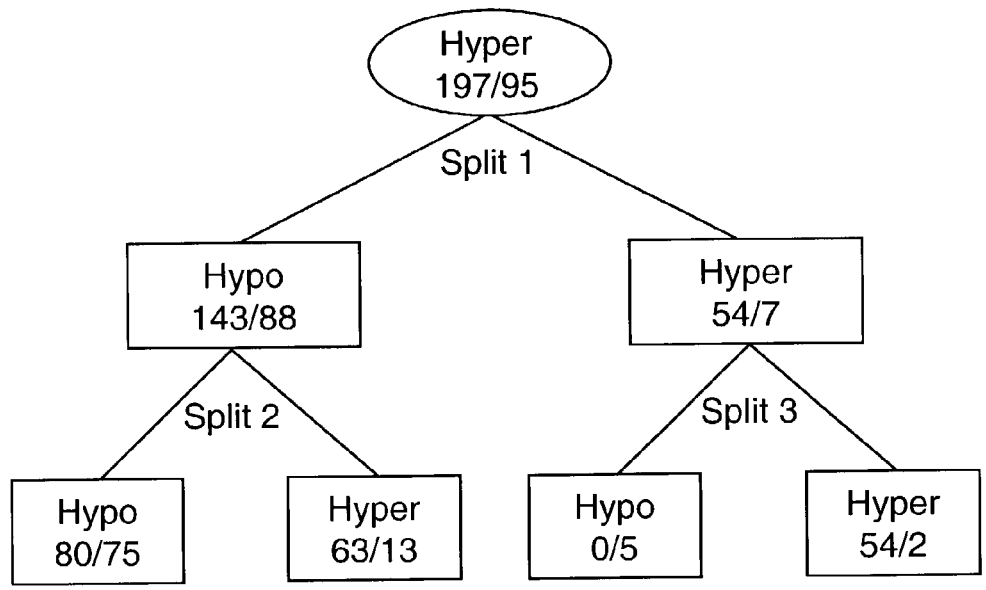
FIG. 11 exemplifies an optimal tree model of FIG. 1 with SAPPHIRe data.

After growing a sufficiently large tree and pruning it back, the final tree looks like what is illustrated in FIG. 11. In each node, the number on the left of the slash is the number of hypertensive cases and the one on the right is the number of hypotensive cases. The outcome class assigned to each node is the final label of that node if it were a terminal one. Since misclassifying a hypotensive case costs twice as misclassifying a hypertensive one, in some nodes, although the proportion of hypertensive cases is higher, the final label is still "Hypo".

Tables 14 and 15 list the detailed information of node-specific variable ranking for Split 2 and Split 3, respectively (SNP for non-wild-type). "R" inside the parenthesis means "risk factor" for hypertension and "P" means "protective factor".

TABLE 14

| Variable | p-value |
|---|---|
| AGTG6A(R) | 0.002 |
| Insulin Resistance (+, R) | 0.007 |
| Menopausal Status (+, R) | 0.009 |
| PPARG12 (R) | 0.047 |

Permutation T = 5.550

TABLE 15

| Variable | p-value |
|---|---|
| HUT2SNP3 (P) | 0.001 |
| HUT2SNP2 (R) | 0.025 |
| AGT2R2C1333T (R) | 0.037 |

Permutation T = 8.915

The permutation test statistics show that in both splits the outcome has strong or significant (linear) association with the selected variable subsets, and such associations are far from random noise. The p-values show that all the variables being selected in both splits contribute significant effects (p-value<0.05) to the final combinations.

The positive associations between hypertension and being post-menopausal or being insulin resistant are consistent with our previous knowledge. The most significant genetic factors are a series of "HUT2" genes (HUT2SNP2, HUT2SNP3) and a series of "AGT" genes (AGTG6A, AGT2R2C1333T). "HUT2" genes concentrate their effects on the Japanese population while "AGT" genes have effects on the whole sample. The full name for "HUT2" is human urea transporter-2 and it is located on chromosome 18, in particular the 18q region. Urea is the major end product of nitrogen metabolism. Its concentration plays a key rule in regulating the volume of body fluid, which in turn directly influences a person's blood pressure. "AGT" stands for Angiotensinogen receptor-2 and it is located on the X chromosome. Angiotensinogen regulates sodium metabolism. The malfunction of this gene may induce salt-sensitive hypertension. "PPARG12" appears to be important, too. "PPARG" stands for peroxisome proliferator activated receptor gamma2 gene and "12" means pro12Ala polymorphisms. This gene is at 3p25 and has a major role in adipogenesis and variation in obesity level. It is also a key regulator of cellular differentiation, insulin sensitization, atherosclerosis, and cancer. In addition, by increasing adipocyte differentiation and transcribing a series of lipogenic proteins, this gene mutation encourages fat storage. All these can contribute to risk of hypertension. The predictive power of this model on the learning sample (learning sample performance) is listed in Table 16 and 5-fold cross-validation (cross-validation performance) is listed in Table 17.

TABLE 16

| True\Classification | Hyper | Hypo | |
|---|---|---|---|
| Hyper | 117 | 15 | Sensitivity = 117/197 = 0.594 |
| Hypo | 80 | 80 | Specificity = 80/95 = 0.842 |
| | | | Miscost = 80 + 2 × 15 = 110 |

TABLE 17

| True\Classification | Hyper | Hypo | |
|---|---|---|---|
| Hyper | 124 | 37 | Sensitivity = 124/197 = 0.630 |
| Hypo | 73 | 58 | Specificity = 58/95 = 0.610 |
| | | | Miscost = 73 + 2 × 37 = 147 |

$R^{cv} = 0.503$ SE $(R^{cv}) = 0.031$

The predictive power is moderate, indicating a difficult classification problem. In this model, the sensitivity increases moderately while the specificity decreases substantially from the learning sample to cross-validation. Overall, our method is superior to most known methods that generate a single model, in both the learning sample and cross-validation. Although it performs less than some "committee voting" methods, such as MART, the difference is not substantial.

2.2 Results on the Dataset with Missing Information

In this dataset, 597 are hypertensive, and the rest (253) are hypotensive. The number of hypertensive cases is more than twice the number of hypotensive cases. Therefore, a 1:2 cost is still used to prevent classifying most observations to the dominant hypertensive class. That is, misclassifying a hypotensive case costs twice as much as misclassifying a hypertensive case.

Figure 12:
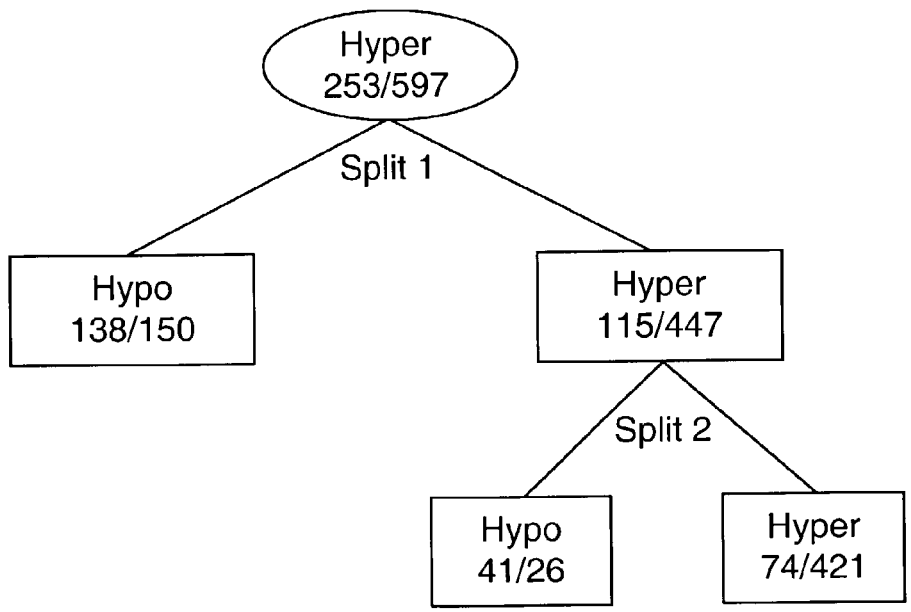
FIG. 12 exemplifies another optimal tree model similar to FIG. 11 with missing information.

The data are first pre-processed by the missing-value-imputation technique described herein, then applied to the main recursive partitioning (splitting) algorithm. The final tree has two splits as shown in FIG. 12. The overall performance of this final model is listed in Table 18 and the cross-validation performance is listed in Table 19.

TABLE 18

| True\Classification | Hyper | Hypo | |
|---|---|---|---|
| Hyper | 421 | 74 | Sensitivity = 421/597 = 0.705 |
| Hypo | 176 | 179 | Specificity = 179/253 = 0.707 |
| | | | Miscost = 176 + 2 × 74 = 324 |

TABLE 19

| True\Classification | Hyper | Hypo | |
|---|---|---|---|
| Hyper | 412 | 101 | Sensitivity = 412/597 = 0.690 |
| Hypo | 185 | 152 | Specificity = 152/253 = 0.601 |
| | | | Miscost = 185 + 2 × 101 = 387 |

$R^{cv} = 0.455$ SE $(R^{cv}) = 0.017$

From Tables 18 and 19, it can be seen that the performance of cross-validation is not far from the performance of the learning sample. The sensitivity remains relatively the same while the specificity deteriorates moderately. Comparisons with other known methods have shown that our approach achieves the highest predictive power in both the learning sample and the cross-validation.

Referring to FIG. 12, node-specific variable ranking for Split 1 and Split 2 is listed in Tables 20 and 21, respectively (SNP, for non-wild-type).

TABLE 20

| Variable | p-value |
|---|---|
| Menopausal Status (+, R) | 4.51e−10 |
| Ethnicity (J, R) | 1.72e−07 |

Permutation T = 31.690

TABLE 21

| Variable | p-value |
|---|---|
| CYP11B2i2INV (R) | 0.0003 |
| CYP2B13 (R) | 0.0008 |
| Insulin Resistance (+, R) | 0.0009 |
| Ethnicity (J, R) | 0.0015 |
| HUT2SNP1 (P) | 0.0057 |
| CYP1B15 (P) | 0.0239 |
| PTP (R) | 0.0295 |
| GNB3 (R) | 0.0854 |
| ACE (R) | 0.0935 |

Permutation T = 10.423

The first split assigns pre-menopausal Chinese women to the left daughter node, labeling them as hypotensive and the rest to the right daughter node for further splitting. The second split focuses on this subgroup of either Japanese or post-menopausal women. It is among these women that the genetic effects show up significantly.

The most important are a series of "CYP" genes, which stands for cytochrome p450. The mutations on such genes affect a group of enzymes, the enzymes that regulate the catalyzation of various redox reactions transforming lipid ligands into inactive metabolites. It has been shown that such mutations will cause replacements of amino acids on some specific locations, and such replacements play an important role in essential hypertension.

Four other important mutations included in the variable subset used to define the second split:

A mutation on "HUT2" (human urea transporter-2) gene, which has been shown significant in the small dataset described heretofore.

A mutation of the "PTP" (protein tyrosine phosphatase) gene, which is a regulator of insulin-like growth factor and has been shown to be linked to insulin secretion dysfunction and to obesity.

A mutation of the "ACE" (angiotensin-converting enzyme) gene. This mutation affects coronary perfusion, increases ventricular hypertrophy and hastens the progression of coronary atherosclerosis.

A mutation on "GNB3": the G protein beta3 polymorphism. Such mutation is associated with enhanced G protein activation and Na(+) exchanger activity. It also has been reported to be associated with obesity and hypertension.

The permutation t-test statistics for both splits are very significant, which indicate a strong signal between the outcome and the variable combinations chosen here. The very strong positive effects (p-value<0.01) of both ethnicity and insulin resistance are also consistent with our previous knowledge.

Implementations

As one skilled in the art would appreciate, the above-described classification and prediction methodology and algorithm can be implemented in any suitable computer language and is not limited to any platform. In an exemplary embodiment, the classification and prediction algorithm is implemented in the R language and was disclosed in the above-referenced provisional application, incorporated herein by reference. The algorithm as implemented in R is a type of reference implementation. R is copyrighted by the GNU Free Software Foundation <<http://www.fsf.org>> and can be downloaded from <<http://www.r-project.org>>.

Figure 13:
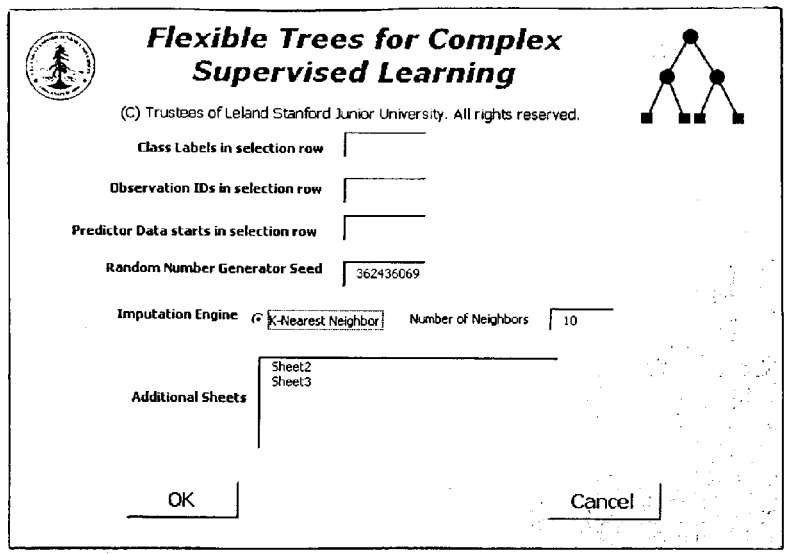
FIG. 13 shows a dialog box of an exemplary user interface for implementing FIG. 1.
Figure 14:
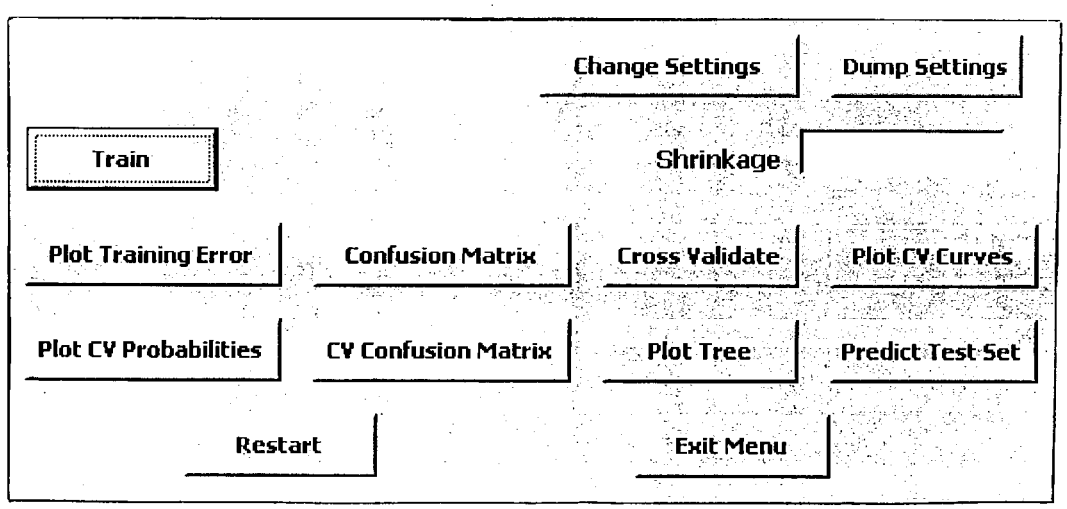
FIG. 14 illustrates an exemplary menu of FIG. 13.

It may be desirable to integrate the classification and prediction algorithm with a user-friendly graphical user interface (GUI). FIG. 13 shows a dialog box of a front-end GUI integrated with a spreadsheet program, which, in this case, is Excel® for Windows® by Microsoft Corp. In the example shown in FIG. 13, data are selected from a spreadsheet and missing data are imputed using an imputation engine, e.g., adaptive nearest neighbor, K-nearest neighbor, etc. FIG. 14 shows a menu box with a plurality of functionality buttons for the GUI shown in FIG. 13. The approach disclosed here can be applied to any supervised learning situation where features are known but outcome is not. If the outcome is disease status or credit worthiness, then this technology can also be used to define high risk groups. This definition can be especially difficult when membership is determined by complex combinations of features. It is in this scenario where our approach seems to shine. An example of how to use this technology comprises the following steps:

1. If there is any missing value in the predictors, use an imputation technique to estimate the missing part. Missing values in the outcome are not allowed.
2. Grow a large tree using the training set.
3. Use either cross-validation or other customer defined test set to find the optimal model complexity, or the appropriate tree size.
4. Using the pruning algorithm to prune the large tree grown in step 1 to the appropriate tree size.
5. Calculate the learning performance, the cross-validation and/or test sample performance.
6. Plot the tree.
7. Get the details of the binary partition for each given split. This information includes:
   (a) which variables are involved;
   (b) how important each variable is;
   (c) what is the specific effect of each variable;
   [(c)] ((d) what is the impurity improvement based on this split;
   [(d)] ((e) how significant is this split; and
   [(e)] ((f) what is the splitting threshold and partition rule.
8. Get the details of each intermediate and terminal node, i.e., the distribution of outcome in each node.
9. Define high risk groups based on the terminal node and the partition information.

Moreover, it can be a very difficult and time consuming task to identify complicated interactions among numerous candidate predictors in order to reveal the true mechanisms that influence the outcome. This is especially true in studies for complicated polygenic diseases, where researchers are trying to detect influential genes from very weak signals. The classification and prediction algorithm provides a new method that combines the strong points of classification trees and regression methods, and treats cumulative effects and complicated interactions simultaneously.

The methodology disclosed herein can be generalized to other studies or areas. The important factors (predictors) detected by the model will help researchers to better understand the etiology and pathology of the disease being studied. The researchers will also be able to narrow down their focus dramatically.

The binary tree model provides a simple diagnostic guideline consisting of questions with only "yes" or "no" answer to the information about the most influential factors, a guideline that is easy to use for most physicians and can serve as an efficient diagnostic tool. Finally, as demonstrated in the examples described herein, the tree-structured model can identify high risk groups based on their genotypes even before the disease occurs and suggest appropriate preventative programs or therapy.

Although the present invention and its advantages have been described in detail, it should be understood that the present invention is not limited to or defined by what is shown or described herein. Known methods, systems, or components may be discussed without giving details, so to avoid obscuring the principles of the invention. As it will be appreciated by one of ordinary skill in the art, various changes, substitutions, and alternations could be made or otherwise implemented without departing from the principles of the present invention. As such, the drawings are for purposes of illustrating a preferred embodiment(s) of the present invention and are not to be construed as limiting the present invention. Accordingly, the scope of the invention should be determined by the following claims and their legal equivalents.

We claim:

1. A method of classifying subjects into classes, wherein the classification is determined by a combination of features of the subjects, the method comprising the steps of:
   a) transforming the features if the features are not quantitative;
   b) transforming the classes with optimal scoring;
   c) regressing the transformed classes with optimal scoring on the transformed features according to a node specific variable ranking of each of the transformed features;
   d) repeating step c) for subsets of the transformed features, from least significant to most, until only one single transformed feature remains, wherein said repeating results in the creation of nested families of the transformed features;
   e) cross-validating the nested families of the transformed features produced by step d);
   f) selecting an optimal subset of the transformed features based on step e);
   g) defining a binary splitting criterion using the optimal subset;
   h) determining whether a significant association exists between membership in a class and the transformed features in the optimal subset;
   i) repeating step c) if the significant association exists; and
   j) assigning subjects to a particular class based on steps a) through i).

2. The method according to claim 1, further comprising the steps of:
   coding the features into dummy indicator variables; and
   coding the classes into dummy indicators.

3. The method according to claim 2, in which the dummy indicator variables are vectors and the dummy indicators are real numbers.

4. The method according to claim 1, in which the features are categorical.

5. The method according to claim 1, in which the features are not categorical.

6. The method according to claim 1, in which the features are selected from the group consisting of ethnicity, mutations at different loci, genotype at selected single nucleotide polymorphisms (snps), age, height, and body mass index.

7. The method according to claim 1, in which the classes are characterized as categorical.

8. The method according to claim 1, in which the classes represents disease status or credit worthiness.

9. The method according to claim 1, in which each of the subsets yields a reduction in generalized Gini index of diversity.

10. The method according to claim 1, further comprising the step of:
determining the node specific variable ranking using a statistic from bootstrap estimates.

11. The method according to claim 1, further comprising the step of:
imputing missing values in the features.

12. The method according to claim 1, in which the significant association exists when a permutation test statistic is larger than a pre-determined threshold.

13. A computer product for implementing the method according to claim 1, the computer product comprising a computer readable medium carrying computer-executable instructions implementing the steps of claim 1.

14. The computer product of claim 13, in which the computer-executable instructions are characterized as R code.

15. A system for classifying subjects into classes, wherein the classification is determined by a combination of features of the subjects, the system comprising:
the computer product of claim 13.

16. A method of using the system of claim 15, comprising the steps of:
imputing any missing values in the features;
growing a large tree using a training data set provided by the system;
using a cross-validation or customized test data set to determine an appropriate tree size;
pruning the large tree to the appropriate tree size;
calculating learning performance and the test data set performance;
plotting the pruned tree;
obtaining binary partition information for each given split in the pruned tree;
obtaining details of each intermediate and terminal node of the pruned tree;
defining high risk groups based on the terminal node and the binary partition information; and
assigning the subjects to high and low risk groups based on said defining.

* * * * *